(12) United States Patent
Sakakita et al.

(10) Patent No.: US 9,254,397 B2
(45) Date of Patent: Feb. 9, 2016

(54) PLASMA EVALUATION APPARATUS

(71) Applicant: NATIONAL INSTITUTE OF ADVANCED INDUSTRIAL SCIENCE AND TECHNOLOGY, Tokyo (JP)

(72) Inventors: Hajime Sakakita, Ibaraki (JP); Yuzuru Ikehara, Ibaraki (JP); Satoru Kiyama, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/359,970

(22) PCT Filed: Oct. 22, 2012

(86) PCT No.: PCT/JP2012/077258
§ 371 (c)(1),
(2) Date: Jul. 11, 2014

(87) PCT Pub. No.: WO2013/077126
PCT Pub. Date: May 30, 2013

(65) Prior Publication Data
US 2014/0312241 A1    Oct. 23, 2014

(30) Foreign Application Priority Data
Nov. 22, 2011  (JP) ................................. 2011-254516

(51) Int. Cl.
*A61B 18/04*    (2006.01)
*A61N 5/10*    (2006.01)
(Continued)

(52) U.S. Cl.
CPC ............ *A61N 5/1064* (2013.01); *A61B 18/042* (2013.01); *H05H 1/0081* (2013.01);
(Continued)

(58) Field of Classification Search
CPC ................... A61B 18/042; A61B 2017/00057; A61B 2018/00642; A61B 2018/00827; A61B 2018/00892; A61N 5/1064; H05H 1/0081
See application file for complete search history.

(56) References Cited

U.S. PATENT DOCUMENTS

| 5,735,846 A | 4/1998 | Panescu et al. |
| 6,565,558 B1 | 5/2003 | Lindenmeier et al. |

(Continued)

FOREIGN PATENT DOCUMENTS

| JP | 06-75070 H | 3/1994 |
| JP | 2002-523173 A | 7/2002 |

(Continued)

OTHER PUBLICATIONS

Grund et al., "Endoscopic Argon Plasma Coagulation (APC) First Clinical Experiences in Flexible Endoscopy", End. Surg., 1994, pp. 42-46, vol. 2, Georg Thieme Verlag Stuttgart, New York.

(Continued)

*Primary Examiner* — Mark R Gaworecki
(74) *Attorney, Agent, or Firm* — Pergament & Cepeda LLP; Milagros A. Cepeda; Edward D. Pergament

(57) ABSTRACT

The present invention provides a plasma evaluation system and method for evaluating plasma, including: a treatment target material and a weak current measurement unit including a resistor unit and a differential amplifier, wherein the treatment target material is connected to the weak current measurement unit via a treatment target side measurement terminal, the resistor unit of the weak current measurement unit is connected to a ground side of a plasma generation current source, and the system and method evaluate plasma by receiving plasma generated by a plasma treatment equipment with the treatment target material, measuring a current by measuring a voltage across resistors of the resistor unit through the differential amplifier, and measuring an output voltage of the plasma generation power source.

13 Claims, 5 Drawing Sheets

(51) Int. Cl.
*H05H 1/00* (2006.01)
*A61B 18/00* (2006.01)
*A61B 17/00* (2006.01)

(52) U.S. Cl.
CPC .................. *A61B2017/00057* (2013.01); *A61B 2018/00642* (2013.01); *A61B 2018/00827* (2013.01); *A61B 2018/00892* (2013.01)

(56) References Cited

U.S. PATENT DOCUMENTS

2005/0263247 A1   12/2005   Samukawa et al.
2010/0231194 A1*   9/2010   Bauch et al. ............... 324/76.52
2013/0204244 A1   8/2013   Sakakita et al.

FOREIGN PATENT DOCUMENTS

JP   2005-340632 A   12/2005
JP   2007-222687 A   9/2007
WO   2012-005132 A1   1/2012

OTHER PUBLICATIONS

International Search Report dated Jan. 22, 2013, for corresponding International Patent Application No. PCT/JP2012/077258.
Extended European Search Report dated May 29, 2015, for corresponding European Patent Application No. EP 12 85 1481.

* cited by examiner

PLASMA EVALUATION APPARATUS

This application is a National Phase application under 35 U.S.C. 371 of International Application No. PCT/JP2012/077258, filed on Oct. 22, 2012 which claims priority to Japanese provisional application No. 2011-254516, filed on Nov. 22, 2011; all of which are hereby incorporated by reference in their entireties.

TECHNICAL FIELD

The present invention relates to a plasma evaluation system.

BACKGROUND ART

Recently, studies for application of plasma generated under atmospheric pressure conditions to medical operations have become active, and development of plasma technologies as medical equipments has been accelerated worldwide. However, introduction of plasma technologies has been being promoted without measurement of characteristics of the plasma to be used, and evaluation of safety of the plasma. In fact, when the energy of the plasma is high, tissues may be damaged.

As characteristics of plasma, electron temperature, electron density, ion temperature, ion density, and space potential have been measured in, particularly, vacuum. Meanwhile, as for non-equilibrium low-temperature plasma under an atmospheric pressure, measurements such as emission spectrometric measurement and electron temperature measurement have just been started. Among the parameters to be measured, the level of the current value to flow through a living body (a human body) is the most influential to the safety. Therefore, it is necessary to measure a current to actually flow, and to control and adjust the plasma treatment equipment.

As common methods for measuring a current, a method of incorporating resistors on a current path, measuring a voltage across the resistors, and evaluating a current based on the resistance values and the voltage value, a method using a Rogowski coil, and a method using a current transformer have been discovered and used traditionally. However, it has not been easy to measure a current of a plasma jet generated by a plasma generation equipment under atmospheric pressure conditions or a current flowing through a living body. The reason is as follows. To generate a non-equilibrium low-temperature plasma under an atmospheric pressure, it is common to fluctuate a plasma generation electrode over time. The current of an electrode of the plasma generation equipment temporally fluctuates at a phase difference from the voltage of the electrode. The current flowing between the voltage application electrode and a ground electrode of the plasma equipment is joined by a current flowing through a living body. The current flowing through the living body has a pulsed shape fluctuating temporally sharply, and there is also a displacement current component to join them, which makes it likely for the voltage applied to the electrode to fluctuate according to the plasma state, which consequently results in fluctuation of the plasma state. In this way, the plasma state, the voltage across the electrodes of the plasma generation equipment, the current between the electrodes of the plasma generation equipment, and the current flowing through the living body are related with each other. Even though it has been possible to measure the current of the supply-side power source of the plasma generation equipment, it has not been easy to separate the current flowing through the living body therefrom, because the current is superposed with the current between the electrodes of the plasma generation equipment.

Hence, the problems are the inability to easily measure and evaluate plasma characteristics of medical plasma treatment equipments expected to spread at home and abroad, and unavailability, particularly at the medical front, of a user-friendly system taking into consideration operability, hygiene, and compactness. That is, there has not been an evaluation system that can maintain and manage the initial performance of the plasma equipments for safety and security, and in addition, it has not been possible to perform a plasma treatment while easily monitoring (measuring or evaluating) the plasma state.

As such, a system and a method for easily measuring and objectively evaluating the state of plasma generated by a plasma treatment equipment, such as those of PTL 1 and NPL 1, under atmospheric pressure conditions have been strongly demanded.

Meanwhile, PTL 2 describes a plasma treatment equipment that, with a photon detecting sensor for measurement of an ultraviolet-induced current provided on a wafer stage, detects an abnormal electrical discharge phenomenon to occur in the plasma chamber real-time simultaneously with an ongoing semiconductor wafer treatment. However, this equipment is an industrial plasma treatment equipment for wafer fabrication, etc. configured to measure a photoelectron current attributable to an abnormal electrical discharge to occur in a region different from a region for a main electrical discharge, and not configured to measure a current to flow through a treatment target of medical plasma treatment equipments, particularly, a living body, etc. Therefore, this equipment can neither be applied to medical purposes, nor used conveniently at the medical front.

CITATION LIST

Patent Literature

PTL 1 PCT/JP2011/064661
PTL 2 Japanese Patent Application Laid-Open (JP-A) No. 2005-340632

Non-Patent Literature

NPL 1 K. E. Grund et al., Endoscope Surgery 2 (1994) 42.

SUMMARY OF INVENTION

Technical Problem

An object of the present invention is to provide a system and a method for easily measuring and evaluating a current of plasma generated by a medical plasma treatment equipment and a current flowing through a living body. Another object of the present invention is to provide an evaluation system that easily monitors the state of an equipment before a plasma treatment and during a plasma treatment at the medical front, etc. Yet another object of the present invention is to provide an evaluation system that can easily check up a plasma treatment equipment for maintenance.

Solution to Problem

To solve the problems described above, a plasma evaluation system of the present invention includes:

a treatment target material; and a weak current measurement unit including a resistor unit and a differential amplifier, wherein the treatment target material is connected to the weak current measurement unit via a treatment target side measurement terminal, wherein the resistor unit of the weak current measurement unit is connected to a ground side of a plasma generation power source, and wherein the plasma evaluation system is configured to evaluate plasma by receiving plasma generated by a plasma treatment equipment with the treatment target material, measuring a current of a voltage across resistors of the resistor unit through the differential amplifier, and measuring an output voltage of the plasma generation power source.

In the plasma evaluation system of the present invention, the resistors of the resistor unit are variable, or resistance values are switchable.

The plasma evaluation system of the present invention is configured to measure an output signal of the differential amplifier and a signal of a voltage by transmitting the signals through an analog optical converter and an optical fiber, converting the signals to electric signals at a light receiving unit, and inputting the electric signals to an analog-digital converter. Alternatively, the plasma evaluation system of the present invention is configured to measure the output signal of the differential amplifier and the signal of the voltage by inputting the signals to the analog-digital converter, further converting the signals to light to thereby transmit the signals through an optical fiber as electrically insulated data, and inputting the signals to another analog-digital converter.

The plasma evaluation system of the present invention is configured to measure a current of the plasma treatment equipment when the treatment target material is a terminal for performance evaluation, measure a current of a small-sized animal such as a mouse when the treatment target material is a tray, with the small-sized animal on the tray, measure a current flowing through a human being or a middle-sized animal when the treatment target material is an examination table, or measure a current flowing through a part of a human body when the treatment target material is an electrode pad.

In the measurement of any of the currents described above, the plasma evaluation system of the present invention is configured to:

(A-1) apply a voltage to the plasma treatment equipment under conditions for not generating plasma, and measure a resulting voltage value V1 and a resulting current value I1;

(A-2) apply a voltage to the plasma treatment equipment under conditions for generating plasma to generate plasma;

(A-3) adjust an output from the supply power source such that a voltage value equal to the voltage value V1 of (A-1) is obtained, and measure a resulting current value I3; and (A-4) adjust the phases of the currents measured in (A-1) and (A-3) to align the peaks of the currents, subtract the current value I1 of (A-1) from the current value I3 of (A-3), and evaluate a resulting value, i.e., I3−I1, as a current component that has actually flowed, or is configured to:

(B-1) apply a voltage to the plasma treatment equipment under conditions for not generating plasma, and measure a resulting voltage value V1 and a resulting current value I1;

(B-2) apply a voltage to the plasma treatment equipment under conditions for generating plasma to generate plasma, and measure a resulting voltage value V2 and a resulting current value I2; and (B-3) adjust the phase of the current measured in (B-1) to align the peak of the current with $(V1/V2) \times I2$, which is obtained by multiplying a ratio between the voltage values of (B-1) and (B-2) by the current of (B-2), subtract I1 from $(V1/V2) \times I2$, and evaluate a resulting value, i.e., $(V1/V2) \times I2 - I1$, in other words, $V1 \cdot I2/V2 - I1$, as a current component that has actually flowed.

The plasma evaluation system of the present invention is configured to measure a current through a Rogowski coil or a current transformer attached between an output of the resistor unit and the ground side of the plasma generation power source.

The plasma evaluation system of the present invention includes:

a treatment target material connected to a ground side of a plasma generation power source via a treatment target side measurement terminal; and a Rogowski coil or a current transformer attached between the treatment target side measurement terminal and the ground side of the plasma generation power source, wherein the plasma evaluation system is configured to evaluate plasma by receiving plasma generated by a plasma treatment equipment with the treatment target material, measuring a current through the Rogowski coil or the current transformer, and measuring an output voltage of the plasma generation power source, and wherein the plasma evaluation system is configured to measure a current of the plasma treatment equipment when the treatment target material is a terminal for performance evaluation, measure a current of a small-sized animal such as a mouse when the treatment target material is a tray, with the small-sized animal on the tray, measure a current flowing through a human being or a middle-sized animal when the treatment target material is an examination table, or measure a current flowing through a part of a human body when the treatment target material is an electrode pad.

The plasma evaluation system of the present invention is configured to measure an output signal of an amplifier of the Rogowski coil or the current transformer by inputting the output signal to an analog-digital converter, or to measure the output signal of the amplifier by transmitting the output signal through an analog optical converter and an optical fiber, converting the output signal to an electric signal at a light receiving unit, and inputting the electric signal to the analog-digital converter, or to measure the output signal of the amplifier by inputting the output signal to the analog-digital converter, further converting the output signal to light to thereby transmit the output signal through an optical fiber as electrically insulated data, and inputting the output signal to another analog-digital converter.

The plasma evaluation system of the present invention includes monitoring with a visible-range or infrared-range camera, which is used in combination with the plasma evaluation system, wherein the plasma evaluation system is configured to observe a state of a portion treated with plasma.

A plasma evaluation method of the present invention includes evaluating atmospheric pressure plasma by measuring a current with the plasma evaluation system described above.

A plasma evaluation method of the present invention is a plasma evaluation method for evaluating atmospheric pressure plasma beforehand by measuring a current beforehand with the plasma evaluation system described above in which a terminal for performance evaluation is selected as the treatment target material, the method including:

evaluating atmospheric pressure plasma by measuring a current within a range in which a relative position of the terminal for performance evaluation with respect to plasma is within an imaginary circular columnar region having a radius of L0×2 and a height of L0×3, wherein L0 is a length of plasma generated by the plasma treatment equipment, and plasma treatment is applied along a center axis of the circular columnar region from a center of an upper base of the circular columnar region toward a lower base thereof.

Advantageous Effects of Invention

Because the plasma evaluation system of the present invention has the configuration described above, it is possible to provide a system and a method for accurately measuring and objectively evaluating a current of plasma generated by a plasma treatment equipment for medical purposes, etc., and a current flowing through a living body, etc. It is also possible to provide a system that easily monitors a state of plasma generated by an equipment before a plasma treatment and during a plasma treatment at the medical front. Further, it is possible to provide an evaluation system that can easily check up a plasma treatment equipment for maintenance. Particularly, the present invention is also effective in making it possible to capture as a change of a current, a state of plasma treatment-induced blood coagulation that is different from treatment target to treatment target, and objectively evaluate the state of the blood coagulation.

DESCRIPTION OF EMBODIMENTS

Figure 1:
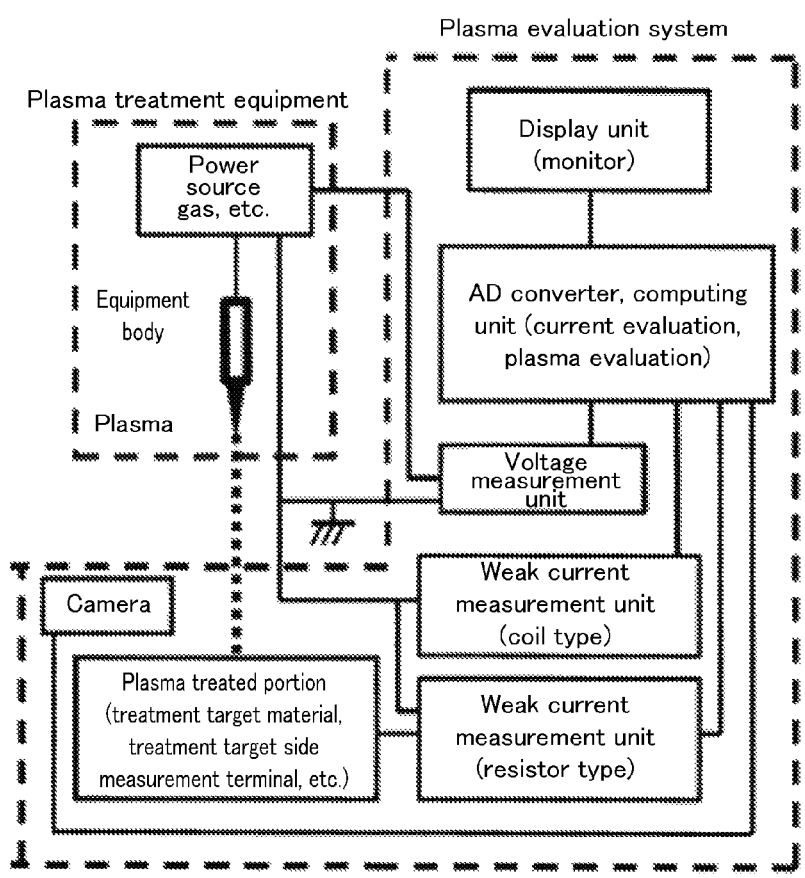
FIG. 1 is a conceptual diagram of the present invention.

To solve the problems, a plasma evaluation system of the present invention is mainly configured to precisely measure and objectively evaluate a current of an atmospheric pressure plasma and a small current having a low frequency or a high frequency flowing through a living body, etc., by employing a method of measuring a voltage across resistors incorporated on a current path as shown in FIG. 1 and evaluating a current based on the resistance values and a voltage value, and a method using a Rogowski coil or a current transformer.

EXAMPLES

Example 1

The present invention will be specifically explained below based on Examples.

Figure 2:
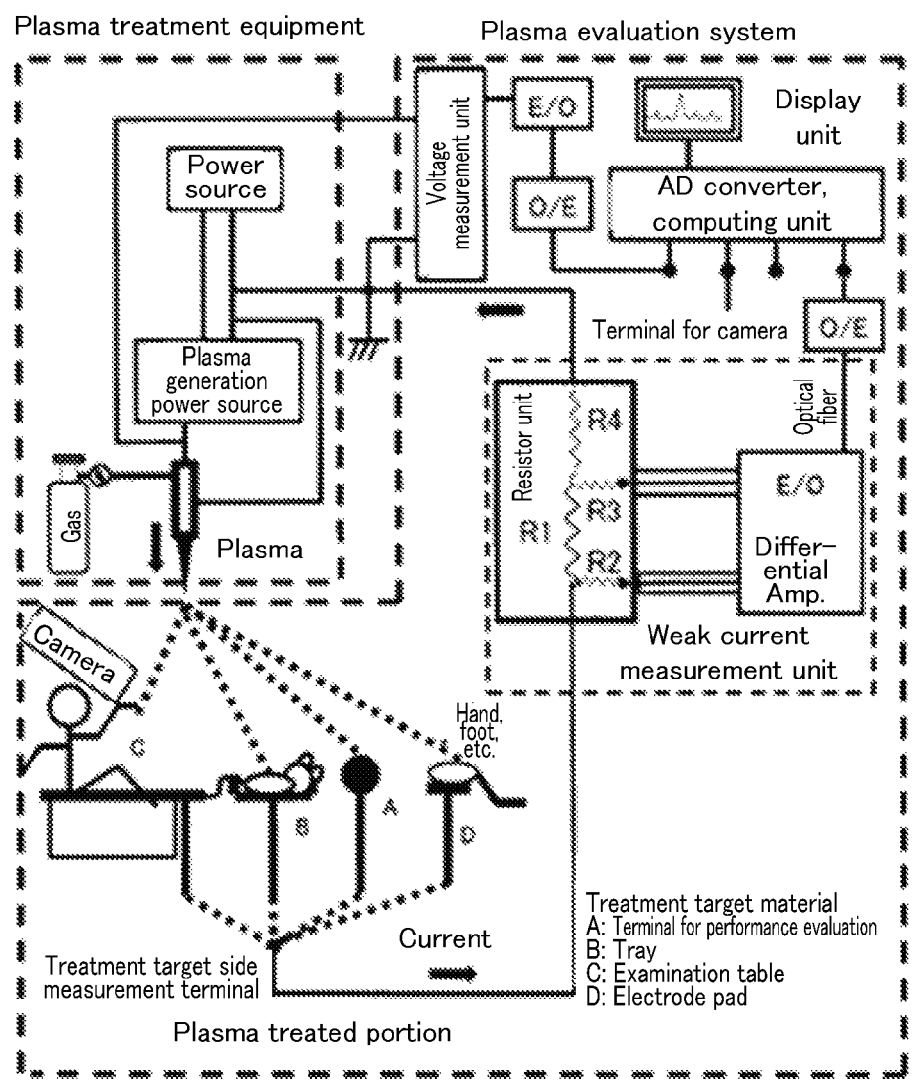
FIG. 2 is an explanatory diagram showing Example 1 of the present invention.

In the plasma evaluation system, a treatment target material receives plasma generated by a plasma treatment equipment, the treatment target material is connected to a weak current measurement unit including a resistor unit and a differential amplifier via a treatment target side measurement terminal, and the weak current measurement unit is connected to a ground side of a plasma generation power source (PS), as shown in FIG. 2. The plasma evaluation system evaluates a current by measuring a voltage across the resistors of the resistor unit through the differential amplifier. It is also possible to measure a change in an output voltage of the plasma generation power source, by using in combination a voltage measurement unit operating based on partial resistance. The ground side of the plasma generation power source is basically grounded, but may be used un-grounded.

The resistors of the resistance unit are variable. Or, the resistance values are switchable. For example, in FIG. 2, R1 is in a resistance value range of from 0.1 to about 1 [k·Ω], R2 and R3 are resistance values of about 50[Ω], and R4 is a resistance value of about 5[Ω].

Any electric signal such as an output from the differential amplifier is input as is to an analog-digital (AD) converter such as an oscilloscope, or transmitted through an analog optical converter and an optical fiber in an electrically insulated state, converted to an electric signal at a light receiving unit, and input to an analog-digital converter such as an oscilloscope. An output is displayed on a monitor unit of the oscilloscope. The data may also be connected to a personal computer and displayed on a monitor of the personal computer. The output from the oscilloscope may also be optically converted to be transmitted through an optical fiber in an electrically insulated state, and converted again to an electric signal to be displayed on a personal computer.

The plasma generation power source is supplied with electricity from a power source such as a DC power source and a battery. A DC power source supplies electricity from an AC line through an isolation transformer. The differential amplifier, the optical converter (from electricity to light; E/O, and from light to electricity; O/E), the oscilloscope, the personal computer, the analog-digital converter, a computing unit, etc. described in the paragraph 0016 are also supplied with electricity from an AC line through an isolation transformer, respectively.

When the treatment target material shown in FIG. 2 is a terminal for performance evaluation (A), a current of each plasma treatment equipment is measured for performance evaluation. When the treatment target material is a tray (B), a small-sized animal such as a mouse is put on the tray, and a current is measured from it. When the treatment target material is an examination table (C), a current flowing through a middle-sized animal such as a human being is measured. When the treatment target material is an electrode pad (D), a current flowing through a part of a human body (a hand, a foot, etc.) is measured. Treatment target materials such as A to D described above are provided as option members to be connected to the treatment target side measurement terminal of the evaluation system body. Treatment target materials such as A to D are selected from a metal, an insulating material (a dielectric material), etc. The shape of the terminal for performance evaluation (A) is selected from a flat plate, a sphere, a hemispherical concave, a sharp shape, etc.

By changing the material of the treatment target material among metals, insulating materials (dielectric materials), etc., it is possible to measure currents by taking advantage of electrical discharge characteristics that depend on the electrical characteristics of the respective materials such as the degree of electrical conductivity and the degree of specific permittivity, or their frequency dependency.

By changing the shape of the treatment target material among a flat plate, a sphere, a hemispherical concave, a sharp shape, etc., it is possible to measure currents by taking advantage of electrical discharge characteristics that depend on the electric field distributions dependent on the respective shapes. For example, of treatment target materials made of the same metal, a treatment target material having a sharp tip is electrically charged intensively at the tip, whereas a treatment target material having a concave surface has an extremely low charge density in the surface. Therefore, it is possible to evaluate plasma of the plasma treatment equipment under different electrical discharge conditions.

It is also possible to monitor a portion treated with plasma with a visible-range or infrared-range camera and send an output signal to a personal computer or the like to thereby display changes in the current, videos and surface temperature of the treated portion, etc. on a monitor.

Example 2

Figure 3:
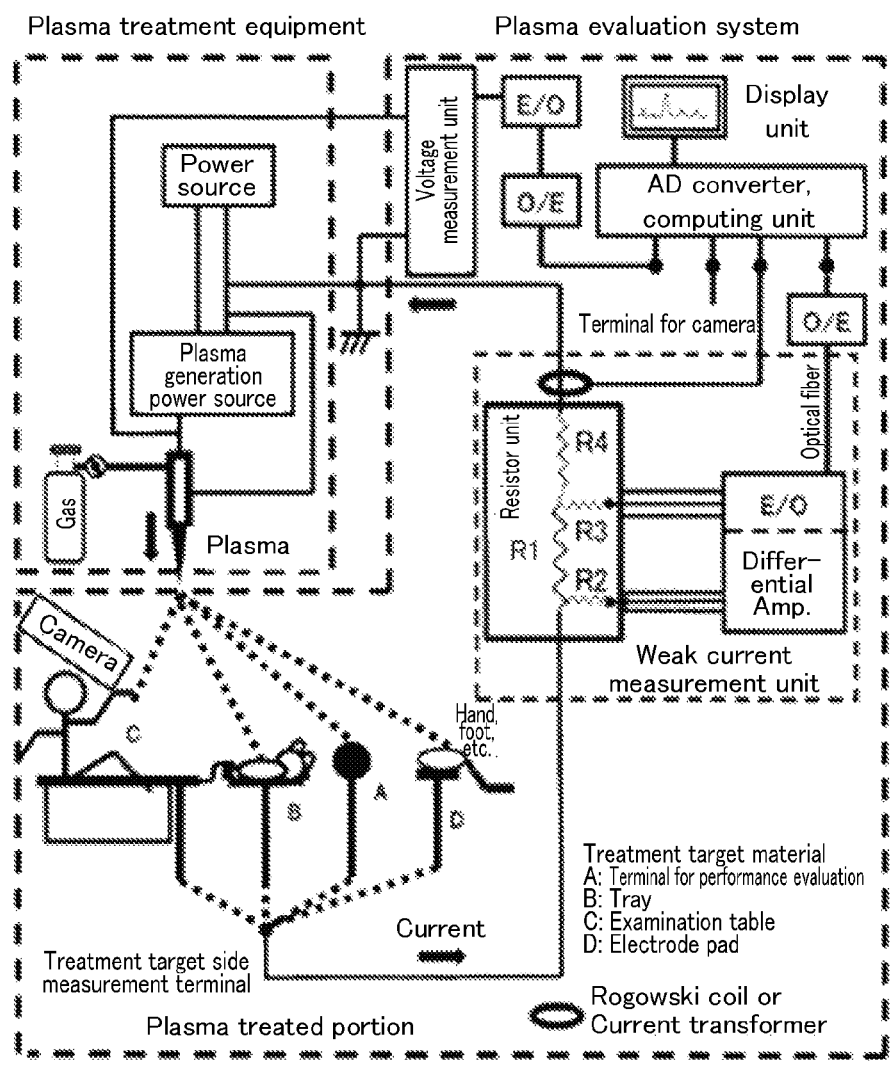
FIG. 3 is an explanatory diagram showing Example 2 of the present invention.

It is also possible to measure a current through a Rogowski coil or a current transformer attached between the output of the resistor unit and the ground side of the plasma generation power source as shown in FIG. 3. An output from the Rogowski coil and the current transformer is amplified by an amplifier and input to an analog-digital converter. It is also possible to measure a signal from an amplifier by optically converting it to transmit it through an optical fiber in an electrically insulated state, converting it to an electric signal at a light receiving unit, and inputting the electric signal to an analog-digital converter. Each amplifier is supplied with electricity from an AC line through an isolation transformer. By attaching the Rogowski coil or the current transformer between the plasma generation power source and a voltage application electrode of the plasma treatment equipment or between a ground electrode of the plasma treatment equipment and the ground side of the plasma generation power source, it is possible to measure currents flowing through these positions.

Example 3

Figure 4:
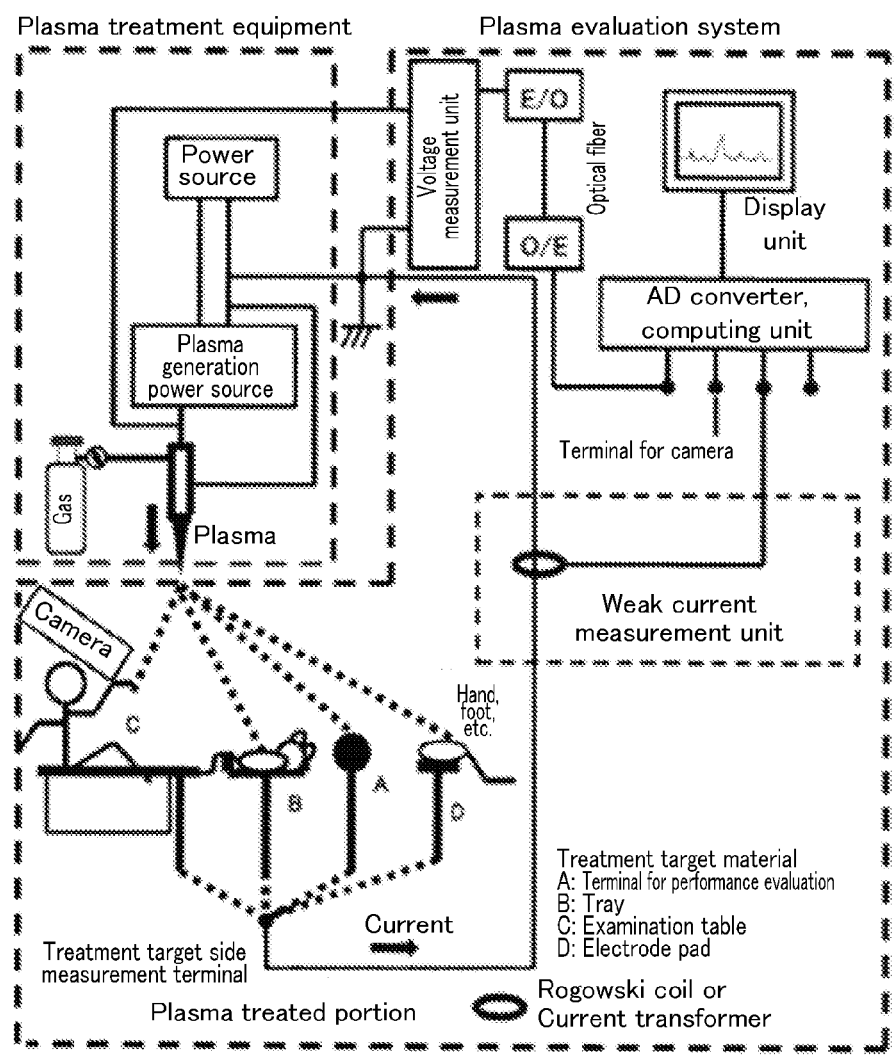
FIG. 4 is an explanatory diagram showing Example 3 of the present invention.

In another configuration, plasma generated by a plasma treatment equipment is received by a treatment target material, and the treatment target material is connected to a ground side of a plasma generation power source via a treatment target side measurement terminal, as shown in FIG. 4. A current can be measured through a Rogowski coil or a current transformer attached between the treatment target side measurement terminal and the ground side of the plasma generation power source.

When evaluating the performance of each plasma treatment equipment by measuring a current with Examples 1 to 3 described above, it is possible to suppress noise signals more by installing a power source for the plasma treatment equipment and the components of the plasma evaluation system other than the plasma treatment target material thereof in electromagnetic shield boxes respectively.

An example of plasma current evaluation will be described. With a signal captured into an analog-digital converter, an oscilloscope, or a personal computer, a state of temporal changes of a current or a voltage is displayed. When the analog-digital converter, the oscilloscope, and the personal computer include a computing function, they can calculate and display the true plasma current component flowed through a living body, etc. by eliminating a displacement current component generated by the plasma generation power source, etc. A specific method is based on the two diagrams described below, including a computing diagram A and a computing diagram B.

<Computing Diagram A>

(1) Conditions for not generating plasma are set (e.g., when not flowing a gas, the plasma equipment is disconnected from the ground electrode).

Then, a voltage is applied to the plasma treatment equipment, and a voltage value V1 and a current value I1 are measured.

(2) Conditions for generating plasma are set (e.g., a gas is let to flow), and a voltage is applied to the plasma treatment equipment to generate plasma.

(3) The output of a supply power source is adjusted to obtain a voltage value equal to the voltage value V1 of (1), and a resulting current value I3 is measured.

(4) The phases of the currents measured in (1) and (3) are adjusted to align the peaks of the currents.

Then, to obtain a current component that has actually flowed through the living body, etc., the current value I1 of (1) is subtracted from the current value I3 of (3) (i.e., I3−I1). In this way, the current component that has actually flowed through the living body, etc. is calculated.

<Computing Diagram B>

(1) Conditions for not generating plasma is set (e.g., when not flowing a gas, the plasma equipment is disconnected from the ground electrode).

Then, a voltage is applied to the plasma treatment equipment, and a voltage value V1 and a current value I1 are measured.

(2) Conditions for generating plasma are set (e.g., a gas is let to flow), a voltage is applied to the plasma treatment equipment to generate plasma, and a voltage value V2 and a current value I2 are measured.

(3) The ratio between the voltage values of (1) and (2) is multiplied by the current of (2), i.e., (V1/V2)×I2.

Then, to align the peak of the current measured in (1) with this, the phase of the current is adjusted, and I1 is subtracted from this. In this way, a current component that has actually flowed through the living body, etc. is calculated. That is, the current component that has actually flowed through the living body, etc. is calculated from (V1/V2)×I2−I1=V1·I2/V2−I1.

Figure 5A:
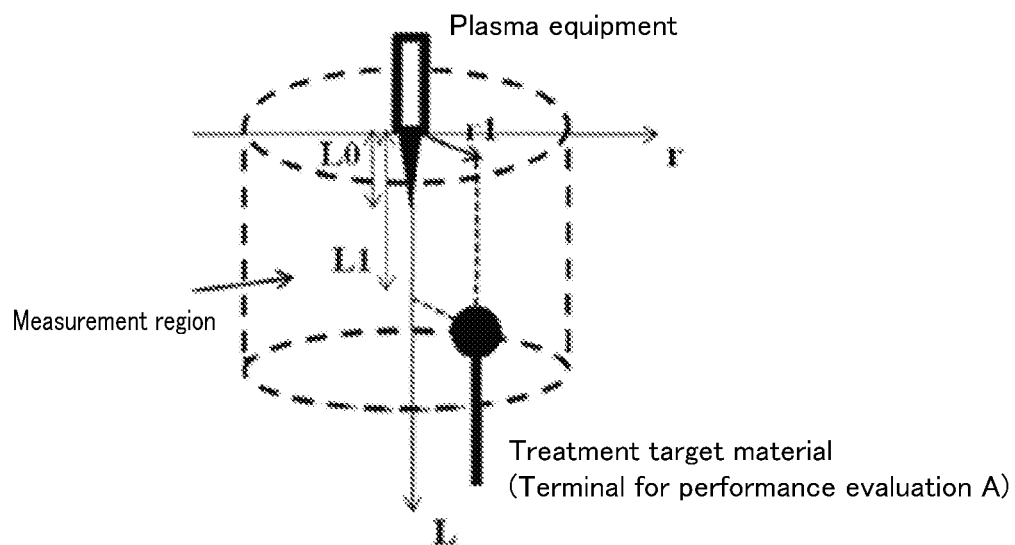
FIG. 5A is a diagram explaining a positional relationship between a terminal for performance evaluation and plasma when evaluating atmospheric pressure plasma by measuring a current using the terminal for performance evaluation as an treatment target material.
Figure 5B:
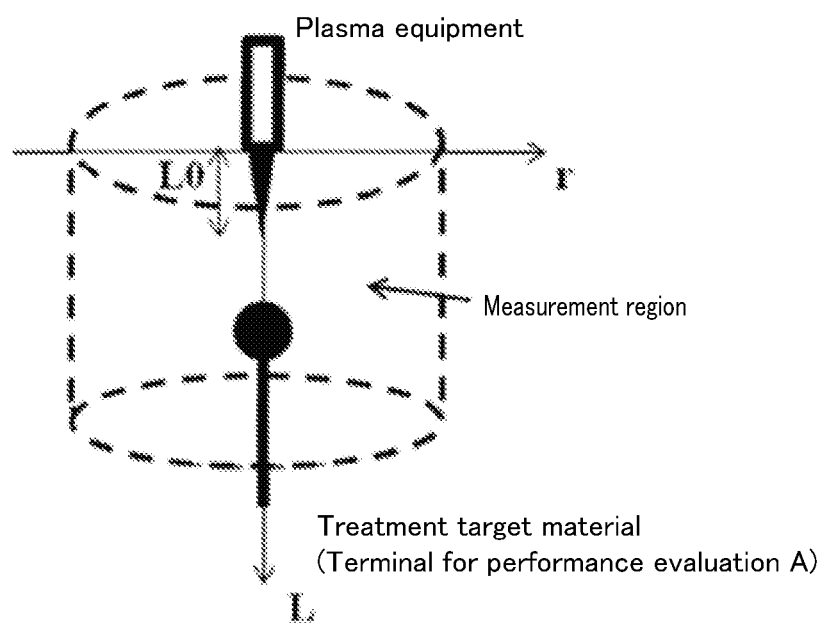
FIG. 5B is a diagram explaining a positional relationship between a terminal for performance evaluation to be measured along an axis and plasma.

FIG. 5A and FIG. 5B are diagrams explaining a plasma evaluation method for evaluating an atmospheric pressure plasma by measuring a current with the plasma evaluation system in which a terminal for performance evaluation is selectively employed as the treatment target material. To develop a method for evaluating a plasma jet, a current of a plasma jet or a weak current flowing in the vicinity thereof during a plasma treatment was examined, and as a result, the following findings were obtained about the relative positional relationship between the plasma jet for atmospheric pressure plasma evaluation based on current measurement and the terminal for performance evaluation.

On the axis of the plasma jet (in a direction L):

(1) A region from the plasma jet outlet of the plasma treatment equipment up to L0 is within the plasma jet ($0 \leq L1 \leq L0$), and this region is influenced the most by the plasma jet. The plasma treatment is performed within this range. Therefore, this region is the most important for evaluating the plasma.

(2) A region from the tip of the plasma jet up to a distance of 2L0 ($L0 < L1 \leq 3L0$) is relatively close to the plasma jet extending by a length of L0, and the influence of the plasma jet (a current passed through the plasma jet) cannot be ignored up to this distance. Information of a current in the vicinity of the plasma jet can be obtained from outside the plasma jet.

(3) When $3L0 < L1$, the influence of the plasma jet is too small. Therefore, information about the plasma jet cannot be obtained at this position, and this position is not suitable for plasma evaluation. Therefore, on the axis of the plasma jet (in the direction L), the range of $0 \leq L1 \leq 3L0$ is suitable for measurement.

In a direction perpendicular to the axis of the plasma jet (in a direction r), (4) The plasma jet has a certain diameter, which however is much smaller than L0. Therefore, the plasma jet can be regarded as a line. A region extending from the axis up to 2L0 ($0 \leq r1 \leq 2L0$), in which the plasma jet having the length L0 has a large view angle, is a region close to the plasma jet in the direction r, and the influence of the plasma jet (a current passed through the plasma jet) cannot be ignored up to this distance. Information of a current in the vicinity of the plasma jet can be obtained from outside the plasma jet. Since the treatment target terminal for performance evaluation has a size, it may be necessary to shift the direction of the plasma jet to some degree. Even in such a case, the reach of the influence of the plasma jet falls within the range of $0 \leq r1 \leq 2L0$ from the axis.

In FIG. 5A and FIG. 5B, a circular columnar region having a radius of L0×2 and a height of L0×3 is assumed (represented by a dotted line in the drawings), where L0 is the length of the plasma generated by the plasma treatment equipment. Plasma treatment is applied along the center axis of the circular column from the center of the upper base of the circular column toward the lower base thereof. In this case, it is possible to evaluate the atmospheric pressure plasma by measuring a current by selecting a measuring position appropriately within the range of the circular columnar region or by shifting the measuring position within the range of the circular columnar region. For example, it is possible to evaluate the optimum state of the plasma treatment equipment, by applying this system to the equipment before use.

For the medical field where a plasma treatment is applied to a living body for the purposes of blood coagulation, blood stanching, etc., an evaluation system is provided, which has a function of monitoring a treatment state when the plasma treatment equipment is used during a plasma treatment, or the performance of the treatment equipment before a treatment or during a treatment.

Because the plasma evaluation system can measure current values generated by plasma treatment equipment, it is possible, for, for example, medical purposes, to give an evaluation to, for example, take a measure of limiting the output when the current value exceeds a certain value.

INDUSTRIAL APPLICABILITY

The present invention can easily measure current components generated by various plasma treatment equipments, and can objectively evaluate the difference between the currents of the equipments. Particularly, the present invention is suitable for measuring medical plasma treatment equipments. Further, when a plasma treatment equipment is used on site such as a factory, by objectively evaluating the state of the plasma treatment equipment, it is possible to perform measurement on site, or perform measurement for maintenance, or objectively judge whether the cause of any trouble is attributable to the plasma equipment or to any other factor.

The invention claimed is:

1. A plasma evaluation system, comprising:
   a treatment target material; and
   a weak current measurement unit including a resistor unit and a differential amplifier,
   wherein the treatment target material is connected to the weak current measurement unit via a treatment target side measurement terminal,
   wherein the resistor unit of the weak current measurement unit is connected to a ground side of a plasma generation power source,
   wherein the plasma evaluation system is configured to evaluate plasma by receiving plasma generated by a plasma treatment equipment with the treatment target material, measuring a current of a voltage across resistors of the resistor unit through the differential amplifier, and measuring an output voltage of the plasma generation power source, and
   wherein the plasma evaluation system is configured to measure an output signal of the differential amplifier and a signal of a voltage by transmitting the signals through an analog optical converter and an optical fiber, converting the signals to electric signals at a light receiving unit, and inputting the electric signals to an analog-digital converter, or to measure an output signal of the differential amplifier and a signal of a voltage by inputting the signals to an analog-digital converter, further converting the signals to light to thereby transmit the signals through an optical fiber as electrically insulated data, and inputting the signals to another analog-digital converter.

2. The plasma evaluation system according to claim 1, wherein the resistors are variable, or resistance values are switchable.

3. The plasma evaluation system according to claim 1, wherein the plasma evaluation system is configured to measure a current of the plasma treatment equipment when the treatment target material is a terminal for performance evaluation, measure a current of a small-sized animal such as a mouse when the treatment target material is a tray, with the small-sized animal on the tray, measure a current flowing through a human being or a middle-sized animal when the treatment target material is an examination table, or measure a current flowing through a part of a human body when the treatment target material is an electrode pad.

4. The plasma evaluation system according to claim 3, wherein in measuring the currents, the plasma evaluation system is configured to:
(A-1) apply a voltage to the plasma treatment equipment under conditions for not generating plasma, and measure a resulting voltage value V1 and a resulting current value I1;
(A-2) apply a voltage to the plasma treatment equipment under conditions for generating plasma to generate plasma;
(A-3) adjust an output from a supply power source such that a voltage value equal to the voltage value V1 of (A-1) is obtained, and measure a resulting current value I3; and
(A-4) adjust phases of the current values measured in (A-1) and (A-3) to align peaks of the current values, subtract the current value I1 of (A-1) from the current value I3 of (A-3), and evaluate a resulting value, which is I3−I1, as a current component that has actually flowed,
or is configured to:
(B-1) apply a voltage to the plasma treatment equipment under conditions for not generating plasma, and measure a resulting voltage value V1 and a resulting current value I1;
(B-2) apply a voltage to the plasma treatment equipment under conditions for generating plasma to generate plasma, and measure a resulting voltage value V2 and a resulting current value I2; and (B-3) adjust a phase of the current value measured in (B-1) to align a peak of the current value with (V1/V2)×I2, which is obtained by multiplying a ratio between the voltage values of (B-1) and (B-2) by the current value of (B-2), subtract I1 from (V1/V2)×I2, and evaluate a resulting value (V1/V2)×I2−I1, which is V1·I2/V2−I1, as a current component that has actually flowed.

5. The plasma evaluation system according to claim 3,
wherein the terminal for performance evaluation, which is the treatment target material, has a shape selected from a flat plate, a sphere, a hemispherical concave, and a sharp shape, and is made of a material selected from a metal and an insulating material (a dielectric material), and
wherein the plasma evaluation system is capable of evaluating plasma of the plasma treatment equipment by measuring a current with the terminal for performance evaluation.

6. The plasma evaluation system according to claim 1,
wherein the plasma evaluation system is configured to measure a current through a Rogowski coil or a current transformer attached between an output of the resistor unit and the ground side of the plasma generation power source.

7. The plasma evaluation system according to claim 1,
wherein the plasma evaluation system is configured to be used in combination with monitoring with a visible-range or infrared-range camera, to observe a state of a portion treated with plasma.

8. A plasma evaluation system, comprising:
a treatment target material connected to a ground side of a plasma generation power source via a treatment target side measurement terminal; and
a Rogowski coil or a current transformer attached between the treatment target side measurement terminal and the ground side of the plasma generation power source,
wherein the plasma evaluation system is configured to evaluate plasma by receiving plasma generated by a plasma treatment equipment with the treatment target material, measuring a current through the Rogowski coil or the current transformer, and measuring an output voltage of the plasma generation power source,
wherein the plasma evaluation system is configured to measure a current of the plasma treatment equipment when the treatment target material is a terminal for performance evaluation, measure a current of a small-sized animal such as a mouse when the treatment target material is a tray, with the small-sized animal on the tray, measure a current flowing through a human being or a middle-sized animal when the treatment target material is an examination table, or measure a current flowing through a part of a human body when the treatment target material is an electrode pad, and
wherein the plasma evaluation system is configured to measure an output signal of an amplifier of the Rogowski coil or the current transformer by inputting the output signal to an analog-digital converter, or to measure an output signal of the amplifier by transmitting the output signal through an analog optical converter and an optical fiber, converting the output signal to an electric signal at a light receiving unit, and inputting the electric signal to an analog-digital converter, or to measure an output signal of the amplifier by inputting the output signal to an analog-digital converter, further converting the output signal to light to thereby transmit the output signal through an optical fiber as electrically insulated data, and inputting the output signal to another analog-digital converter.

9. The plasma evaluation system according to claim 8,
wherein the plasma evaluation system is configured to be used in combination with monitoring with a visible-range or infrared-range camera, to observe a state of a portion treated with plasma.

10. The plasma evaluation system according to claim 8,
wherein in measuring the currents, the plasma evaluation system is configured to:
(A-1) apply a voltage to the plasma treatment equipment under conditions for not generating plasma, and measure a resulting voltage value V1 and a resulting current value I1;
(A-2) apply a voltage to the plasma treatment equipment under conditions for generating plasma to generate plasma;
(A-3) adjust an output from a supply power source such that a voltage value equal to the voltage value V1 of (A-1) is obtained, and measure a resulting current value I3; and
(A-4) adjust phases of the current values measured in (A-1) and (A-3) to align peaks of the current values, subtract the current value I1 of (A-1) from the current value I3 of (A-3), and evaluate a resulting value, which is I3-I1, as a current component that has actually flowed,
or is configured to:
(B-1) apply a voltage to the plasma treatment equipment under conditions for not generating plasma, and measure a resulting voltage value V1 and a resulting current value I1;
(B-2) apply a voltage to the plasma treatment equipment under conditions for generating plasma to generate plasma, and measure a resulting voltage value V2 and a resulting current value I2; and
(B-3) adjust a phase of the current value measured in (B-1) to align a peak of the current value with (V1/V2)×I2, which is obtained by multiplying a ratio between the voltage values of (B-1) and (B-2) by the current value of (B-2), subtract I1 from (V1/V2)×I2, and evaluate a resulting value (V1/V2)×I2−I1, which is V1·I2/V2−I1, as a current component that has actually flowed.

11. The plasma evaluation system according to claim 8,
wherein the terminal for performance evaluation, which is the treatment target material, has a shape selected from a flat plate, a sphere, a hemispherical concave, and a sharp shape, and is made of a material selected from a metal and an insulating material (a dielectric material), and
wherein the plasma evaluation system is capable of evaluating plasma of the plasma treatment equipment by measuring a current with the terminal for performance evaluation.

12. A plasma evaluation method, comprising:
evaluating atmospheric pressure plasma by measuring a current with a plasma evaluation system, which comprises:
a treatment target material; and
a weak current measurement unit including a resistor unit and a differential amplifier,
wherein the treatment target material is connected to the weak current measurement unit via a treatment target side measurement terminal,
wherein the resistor unit of the weak current measurement unit is connected to a ground side of a plasma generation power source,
wherein the plasma evaluation system is configured to evaluate plasma by receiving plasma generated by a plasma treatment equipment with the treatment target material, measuring a current of a voltage across resistors of the resistor unit through the differential amplifier, and measuring an output voltage of the plasma generation power source, and wherein the plasma evaluation system is configured to measure an output signal of the differential amplifier and a signal of a voltage by transmitting the signals through an analog optical converter and an optical fiber, converting the signals to electric signals at a light receiving unit, and inputting the electric signals to an analog-digital converter, or to measure an output signal of the differential amplifier and a signal of a voltage by inputting the signals to an analog-digital converter, further converting the signals to light to thereby transmit the signals through an optical fiber as electrically insulated data, and inputting the signals to another analog-digital converter.

13. The plasma evaluation method according to claim 12, for evaluating atmospheric pressure plasma by measuring a current beforehand with a terminal for performance evaluation selected as the treatment target material, the method comprising:

evaluating atmospheric pressure plasma by measuring a current within a range in which a relative position of the terminal for performance evaluation with respect to the plasma is within an imaginary circular columnar region having a radius of L0×2 and a height of L0×3, wherein L0 is a length of the plasma generated by a plasma treatment equipment, and plasma treatment is applied along a center axis of the circular columnar region from a center of an upper base of the circular columnar region toward a lower base thereof.

* * * * *